(12) United States Patent
Mellet et al.

(10) Patent No.: US 10,421,725 B2
(45) Date of Patent: Sep. 24, 2019

(54) ALKOXYAMINES FOR THE TREATMENT OF CANCERS

(71) Applicants: Centre National De La Recherche Scientifique, Paris (FR); Universite d'Aix Marseille, Marseilles (FR); Universite de Bordeaux, Bordeaux (FR)

(72) Inventors: Philippe Mellet, Bordeaux (FR); Sylvain Marque, Antraigues-sur-volanes (FR); Jean-Michel Franconi, Merignac (FR); Pierre Voisin, Cestas (FR); Damien Moncelet, Bordeaux (FR); Paul Bremond, Marseilles (FR); Gérard Audran, Marseilles (FR)

(73) Assignees: Centre National de la Recherche Scientifique, Paris (FR); Universite d'aix Marseille, Marseilles (FR); Universite de Bordeaux, Bordeaux (FR)

( * ) Notice: Subject to any disclaimer, the term of this patent is extended or adjusted under 35 U.S.C. 154(b) by 746 days.

(21) Appl. No.: 14/897,600

(22) PCT Filed: Jun. 13, 2014

(86) PCT No.: PCT/IB2014/062220
§ 371 (c)(1),
(2) Date: Dec. 10, 2015

(87) PCT Pub. No.: WO2015/001436
PCT Pub. Date: Jan. 8, 2015

(65) Prior Publication Data
US 2016/0115130 A1 Apr. 28, 2016

(30) Foreign Application Priority Data

Jun. 17, 2013 (EP) .................................. 13305815

(51) Int. Cl.
*A61K 9/00* (2006.01)
*C07D 213/30* (2006.01)
(Continued)

(52) U.S. Cl.
CPC ............ *C07D 213/30* (2013.01); *A61K 49/06* (2013.01); *C07C 239/20* (2013.01); *A61B 5/055* (2013.01); *A61B 5/4848* (2013.01); *C07F 9/58* (2013.01)

(58) Field of Classification Search
CPC ..................................................... C07D 213/30
See application file for complete search history.

(56) References Cited

FOREIGN PATENT DOCUMENTS

WO 2005113566 A1 12/2005

OTHER PUBLICATIONS

Acerbis, Intramolecular Hydogen Bonding: The case of b-Phosphorylated Nitroxide(=Aminoxyl) Radical, Helvetica Chimica Acta, 2006, 89, 2119-2132.*

(Continued)

*Primary Examiner* — Paul W Dickinson
(74) *Attorney, Agent, or Firm* — Christensen O'Connor Johnson Kindness PLLC

(57) ABSTRACT

The present invention relates to alkoxyamines of general formula (I), and to compounds of general formula (IIa), (IIb), (IIc), (IId), IIe), (IIf) or (IIg), as such and for the treatment of cancers.

(I)

(Continued)

-continued

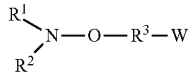 (IIa)

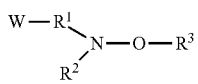

(IIb)

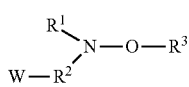

(IIc)

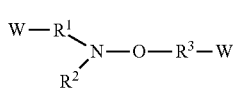

(IId)

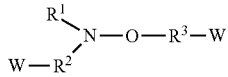

(IIe)

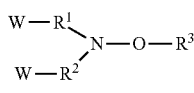

(IIf)

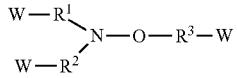

(IIg)

5 Claims, 5 Drawing Sheets

(51) Int. Cl.
  *C07C 239/20* (2006.01)
  *A61K 49/06* (2006.01)
  *A61B 5/055* (2006.01)
  *A61B 5/00* (2006.01)
  *C07F 9/58* (2006.01)

(56) References Cited

OTHER PUBLICATIONS

Bertin, D., et al., "Polar, Steric, and Stabilization Effects in Alkoxyamines C—ON Bond Homolysis: A Multiparameter Analysis," Macromolecules 38(7):2638-2650, Apr. 2005.

Brémond, P., et al., "Chemically Triggered C—ON Bond Homolysis of Alkoxyamines. Quaternization of the Alkyl Fragment," Organic Letters 14(1):358-361, Jan. 2012.

Leroi, C., et al., "Alkoxyamine Mediated Radical Synthesis of Indolinones and Indolines," Organic Letters 5(26):4943-4945, Nov. 2003.

Marque, S., et al., "Factors Influencing the C—O Bond Homolysis of Alkoxyamines: Effects of H—Bonding and Polar Substituents," The Journal of Organic Chemistry 66(4):1146-1156, Feb. 2001.

Marque, S., et al., "Factors Influencing the C—O Bond Homolysis of Trialkylhydroxylamines," Macromolecules 33(12):4403-4410, Jun. 2000.

Molawi, K., et al., "Tin-Free Radical Alkoxyamine Addition and Isomerization Reactions by Using the Persistent Radical Effect: Variation of the Alkoxyamine Structure," Chemistry—A European Journal 11(8):2335-2350, Apr. 2005.

Trofimov, B.A., et al., "Pyrroles from Ketoximes and Acetylene," No. 36. 4, 4, 6, 6-Tetramethyl-4, 5, 6, 7-Tetrahydro-5-Azaindole, Its Nitroxyle and Vinyl Derivatives, and Spin-Labelled Copolymer, Chemistry of Heterocyclic Compounds 24(3):285-289, Mar. 1988.

International Search Report dated Oct. 10, 2014, issued in corresponding International Application No. PCT/IB/2014/062220, filed Jun. 13, 2014, 5 pages.

* cited by examiner

ALKOXYAMINES FOR THE TREATMENT OF CANCERS

The present invention relates to alkoxyamines useful for the treatment of cancers.

For 50 years now, cancer has been a major issue in developed countries. Its occurrence has been steadily increasing due to human behavior (quality of food, nutrition, style of life . . . ), environmental conditions (pollution, chemical aggressions, nuclear accidents . . . ) and population aging. It mobilizes tremendous efforts in many fields: fundamental biology, medical research, drug development, prevention. Despite these efforts, large amounts of funding and many successes in curing, cancer continues to be a problem both in its occurrence and its lethality. Over the last 50 years, chances of recovering from cancer have increased thanks to clinical research and several therapeutic options (surgery, chemo- and radiotherapies). The current trend, however, is to develop more specific drugs with a much higher selectivity between anomalous and healthy cells in vivo [Ozben, T. *J. Pharm. Sci.* 2007, 96, 2181-2196].

Free radical species lead to DNA/proteins/lipids modifications, which in turn initiate cell death when the repairing machinery is overwhelmed by the radical generation; they can be organized in 3 mains families: Reactive Oxygenated Species, ROS (mainly radical species such as superoxide, hydroxyl radical, hydroperoxyl radicals, and the second generation alkoxyl and alkylperoxyl radicals), Reactive Nitrogen Species, RNS (mainly nitrogen oxide, and aminyl radicals), and radicals on DNA, proteins, and lipids, said radicals are generated by the reaction with ROS/RNS or by irradiation (UV or γ-/X-rays irradiation). ROS and RNS are crucial for life but they must be kept under tight control by Anti-Oxidants (AO) [Valko, M. et al. *Int. J. Biochem. Cell Biol.* 2007, 39, 44-84; Azad, M. B. et al. *Antioxid. Redox Signal.* 2009, 11, 777-790]. Unbalanced ROS/AO or RNS/AO ratios may also have lethal effects on cells, through DNA/proteins/lipids radical modifications aforementioned [Valko, M. et al. *Chem.-Biol. Interact.* 2006, 160, 1-40].

Interestingly, recent results indicate that cancer cells show much higher, but still controlled, ROS activity than healthy cells. This gave rise to the idea that increasing the ROS/AO ratio may lead to cancer cell death either by apoptosis or necrosis [Wang, J. et al. *Cancer Biol. Ther.* 2008, 7, 1875-1884 ; Kern, J. C. et al. *Front. Biosci.* 2005, 10, 1727-1738] and removal by phagocytic immune cells. In addition, excess free radical species in cancer cells may lead to protein modifications that trigger immune responses and ultimately cancer cell death [Senovilla, L. et al *Science* 2012, 337, 1678-1684].

Increasing the ROS/AO ratio may therefore be applied as a therapeutic approach if it shows strong selectivity for cancer over healthy cells. The main advantages of such approaches are that the immune system plays an important part and that it is almost independent of the type of cancer [Fruehauf, J. P. et al. *Review of Anticancer Therapy* 2008, 8, 1751-1757; Trachootham, D et al. *Nat. Rev. Drug Discov.* 2009, 8, 579-591]. However, its success relies on very drastic requirements that include carefully controlled generation of radicals in cancer cells, controlled kinetics of their generation, and low cytotoxicity of the radical pro-drugs [Karwa, A. S. et al. *ACS Med. Chem. Lett.* 2011, 2, 828-833].

Based on this, Inventors have developed new molecules allowing the increase of ROS/AO ratio that exhibits therapeutic properties to cure solid tumors and spectroscopic properties to monitor the progress of curing.

The approach of the present invention relies on the triggering of the cellular death by the generation of reactive alkyl radicals from alkoxyamines in the close environment of a tumor.

Alkoxyamines ($R^1R^2NOR^3$) are a versatile family of metastable molecules able to spontaneously homolyse at physiological temperature to a stable nitroxide and a highly reactive alkyl radical. Thus, they can be used as a source of reactive alkyl radicals for killing cancer cells and as a source of nitroxides for monitoring the tumor evolution via Overhauser-enhanced magnetic resonance imaging. To gain specificity, said alkoxyamines may be stabilized as prodrugs by grafting a specific chemical residue sensitive to a chemical, physical or a biochemical signal, for example, a peptide removable by a targeted protease specifically expressed by tumor cells.

Alkoxyamines are well known molecules already used for various applications but these compounds have never been described as showing therapeutic interest; the present invention thus relates to a selection of specific alkoxyamines having the following features:
i) when stabilized as a prodrug, a selective activation of the stabilized alkoxyamines by the specific conditions of the cancer cells environment;
ii) a rapid homolysis of the C—ON bond of the activated alkoxyamine into an alkyl radical ($R^3$.) and a nitroxide ($R^1R^2NO$.);
iii) an activation of the cell death that processes through a local oxidative stress by the short-lived alkyl radicals;
iv) the monitoring of drug release and imaging of the tumor site by sensing the released nitroxide with imaging techniques such as Magnetic Resonance Imaging enhanced by the Overhauser effect (OMRI) or as Electron Paramagnetic Resonance Imaging (EPRI);
v) a potential re-activation of the immune system against the tumour through the alteration of membrane proteins and lipids by radical processes creating non-self determinants and/or by an immunogenic cell death (Galluzzi L, Senovilla L, Zitvogel L, Kroemer G. The secret ally: immunostimulation by anticancer drugs. Nat Rev Drug Discov. 2012 Feb. 3; 11(3):215-33.).

Alkoxyamines presently developed require to be stable enough to be easily handled at room temperature (Bond Dissociation Energy BDE>120 kJ/mol) and able to be activated into highly labile species which release alkyl radicals for therapeutic applications and nitroxides for diagnostic applications.

A first object of the present invention thus relates to a compound of general formula (I):

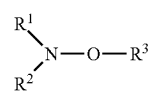

wherein
$R^1$ and $R^2$ which may be identical or different are chosen amongst:
a secondary alkyl group

or a tertiary alkyl group

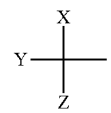

wherein X, Y and Z which may be identical or different are chosen amongst a linear or ramified alkyl radical including short and long carbon chains (1 to 40 carbon atoms), X, Y and/or Z may be substituted by a functional group chosen amongst hydroxyl, amine, mercaptan, azide, halogenure, carbonyl (aldehyde, amide, ketone, acide, ester, and their thio derivatives), aromatic, heteroaromatic (for example pyridine, puric and pyrimidic bases), heterocycles (for example imidazolione), vinyl, alcyne, phosphoryl optionally substituted by a ($C_1$-$C_4$) alkoxy radical;
a 5 to 12 membered ring (heterocyclic or not) which can carry the various functions mentioned above;
wherein $R^1$ and/or $R^2$ are optionally substituted by a stabilizing group or an addressing group W selected from a peptide, a sugar, a steroid, a fatty acid, a polyketones, polyphenols, prostaglandines or a lipid, a bio-receptor or an antigen;
$R^1$ and $R^2$ being different from $R^3$;
$R^3$ is chosen amongst:
(i) a secondary alkyl radical

or a tertiary alkyl radical

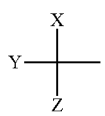

wherein X, Y and Z may be identical or different, X and Z are a linear or ramified alkyl radical including short and long carbon chains (1 to 40 carbon atoms) and may be substituted by a functional group chosen amongst hydroxyl, amine, mercaptan, azide, halogenure, carbonyl (aldehyde, ketone, acide, ester, and their thio derivatives), aromatic, heteroaromatic, heterocycles, vinyl, alcyne; Y is chosen amongst an aromatic group or heteroaromatic group, a carbonyl function optionally in a protected form such as enol, acetate, acetals, enamine, an easily oxidable function, an vinyl, an alkene function including short and long carbon chains (1 to 40 carbon atoms), an alkyne function including short and long carbon chains (1 to 40 carbon atoms), a function thiocarbonyl, a function imine, a function oxime or a function cyano;

(ii)

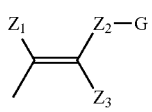

wherein
$Z_1$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—);

$Z_2$ is selected from a single bound, —O—, —S—, —NR—, with R being a linear or ramified $C_1$-$C_{40}$ alkyl radical, a aryl or a heteroaryl group, a linear or ramified $C_1$-$C_{40}$ vinyl radical, a linear or ramified $C_1$-$C_{40}$ alkyne radical, those radicals being optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—);

$Z_3$ is selected from a hydrogen atom; a linear or ramified $C_1$-$C_{40}$ alkyl radical, a linear or ramified $C_1$-$C_{40}$ vinyl radical, a linear or ramified $C_1$-$C_{40}$ alkyne radical, an aryl group, a heteroaryl group, those radicals being optionally interrupted by at least one O, S, NH and optionally substituted by a carbonyl function (—CO—), a thiocarbonyl function (—CS—), an amine or an imine function ((—C(NH)— or —C(N—[$C_1$-$C_4$ alkyl])-), an oxime function (—C(NOH)—);

G is either an hydrogen atom or an addressing or stabilizing group W selected from a peptide, a sugar, a steroid, a fatty acid, a polyketones, polyphenols, prostaglandines or a lipid, a bio-receptor or an antigen;

(iii)

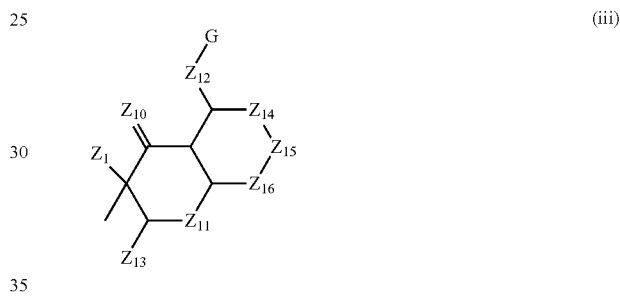

wherein $Z_1$ and G are as described above;
$Z_{10}$ and $Z_{11}$ are independently selected from —O—, —S—, —NR— and —$CR_2$— where R is as defined above;
$Z_{12}$ is selected from —O—, —S— and —NR— where R is as defined above;
$Z_{13}$ is selected from —$OSO_2R$, a halogen atom, an ammonium group, a phosphate group, —$RSO_2$, —OH, —SH, —OR and —SR where R is as defined above;
$Z_{14}$, $Z_{15}$ and $Z_{16}$ are independently selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—);

(iv)

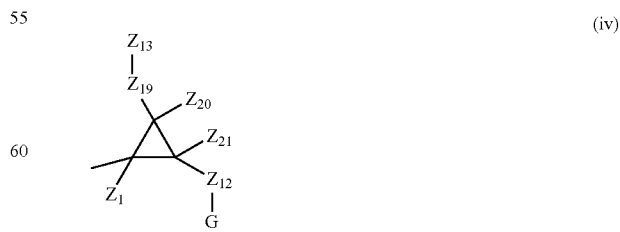

wherein $Z_1$, $Z_{12}$, $Z_{13}$ and G are as described above;
$Z_{19}$ is selected from —$CH_2$—, —CHR— and —$CR_2$— where R is as defined above;

$Z_{20}$ and $Z_{21}$ are independently selected from an hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally interrupted by at least one O, S, NH and optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—).

An easily oxidable function is a group able to bound one or more oxygen atoms or able to release one or more electrons.

In other embodiments, $R^3$ is selected amongst:

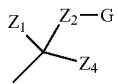

(v)

wherein $Z_1$, $Z_2$ and G are as described previously;
and $Z_4$ is chosen amongst a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—);

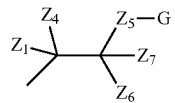

(vi)

wherein $Z_1$, $Z_4$, R and G are as described previously;
$Z_5$ is selected amongst —O—, —S—, —NH— and —NR— where R is as defined above;
$Z_6$ is chosen amongst a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—); and
$Z_7$ is selected from —OR, —SR, —OH and —SH where R is as defined above;

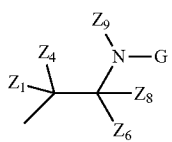

(v)

wherein $Z_1$, $Z_4$, $Z_6$ and G are as described above;
$Z_8$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—); and
$Z_9$ is selected from —H and —R where R is as defined above;

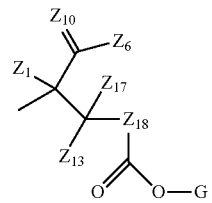

(vi)

wherein $Z_1$, $Z_6$, $Z_{10}$, $Z_{13}$ and G are as described above;
$Z_{17}$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally interrupted by at least one O, S, NH and optionally substituted by a carbonyl function (—CO—), a thiocarbonyl function (—CS—), an amine or an imine function ((—C(NH)— or —C(N—[$C_1$-$C_4$ alkyl])-), an oxime function (—C(NOH)—); an aryl or a heteroaryl group optionally linked to at least one O, S, NH;
$Z_{18}$ is selected from —O—, —S—, —NH—, —NR—, —CH$_2$—, —CHR— and —CR$_2$— where R is as defined above;

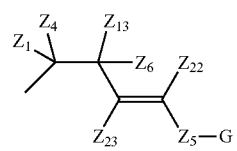

(viii)

wherein $Z_1$, $Z_4$, $Z_5$, $Z_6$, $Z_{13}$ and G are as described above;
$Z_{22}$ and $Z_{23}$ are independently selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—).

"Alkyl" in the sense of the present invention means a linear, branched, or cyclic, saturated or unsaturated, optionally substituted carbon radical containing 1 to 40 carbon atoms. Saturated linear or branched alkyl includes, for example, methyl, ethyl, propyl, butyl, pentyl, hexyl, heptyl, octyl, nonyl, decyl, undecyl, and dodecanyl radicals and their branched isomers. Cyclic alkyl includes cyclopropyl, cyclobutyl, cyclopentyl, cyclohexyl, bicyclo[2.1.1]hexyl, and bicyclo[2.2.1]heptyl radicals. Unsaturated cyclic alkyls include, for example, cyclopentenyl, and cyclohexenyl. Unsaturated alkyls, which are also called "alkenyl" or "alkynyl", contain, respectively, at least one double or triple bond. This may include, for example, ethylenyl, propylenyl, butenyl, pentenyl, hexenyl, acetylenyl, propynyl, butynyl, pentynyl, and hexynyl radicals and their branched isomers.

The term "aryl" denotes, generally, a cyclic aromatic substituent containing from 6 to 20 carbon atoms. In the context of the invention, the aryl group may be mono- or polycyclic. As an indication, the groups phenyl, benzyl, and naphthyl are included. The aryl group may be optionally substituted by one or more hydroxyl groups, one or more alkoxy groups, one or more halogen atoms selected from fluorine, chlorine, bromine, and iodine atoms, one or more nitro groups (—NO$_2$), one or more nitrile groups (—CN), one or more alkyl groups, one or more aryl groups, with the alkoxy, alkyl, and aryl groups as defined in the context of the present invention.

The term "heteroaryl" denotes, generally, a mono- or polycyclic aromatic substituent containing from 5 to 10 members, including at least 2 carbon atoms, and at least one heteroatom selected from nitrogen, oxygen, or sulfur. The heteroaryl group may be mono- or polycyclic. As in indication, the groups furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, triazolyl, pyrazolyl, oxazolyl, isoxazolyl, benzoxazolyl, thiazolyl, benzothiazolyl, isothiazolyl, pyridazinyl, pyrimidinyl, pyrazinyl, triazinyl, cinnolinyl, phtalazinyl, quinazolinyl, 1,1-diphenylhydrazinyl, and 1,2-diphenylhydrazinyl are included. The heteroaryl group may be optionally substituted by one or more hydroxyl groups, one or more alkoxy groups, one or more halogen atoms selected from fluorine, chlorine, bromine, and iodine atoms, one or more nitro groups (—NO$_2$), one or more nitrile groups (—CN), one or more aryl groups, one or more alkyl groups with the alkyl, alkoxy, and aryl groups as defined in the context of the present invention.

The term "alkoxy" signifies an alkyl group, as defined above, which is bonded by an oxygen atom (—O-alkyl).

The term "alkenyl" signifies an alkyl group, as defined above, which contains at least one double bound (—CH═CH—).

The term "alkynyl" signifies an alkyl group, as defined above, which contains at least one double bound (—C≡C—).

The term "heterocycle" denotes, generally, a mono- or polycyclic substituent containing 5 to 10 members, which is saturated or unsaturated and contains from 1 to 4 heteroatoms selected independently of one another from nitrogen, oxygen, and sulfur. As an indication, the substituents morpholinyl, piperidinyl, piperazinyl, pyrrolidinyl, imidazolyl, imidazolidinyl, imidazolinyl, pyrazolidinyl, tetrahydrofuranyl, tetrahydropyranyl, tetrahydropyrimidinyl, triazolyl, pyrazolyl, thianyl, oxazolidinyl, isoxazolidinyl, thiazolidinyl, and isothiazolidinyl are included. The heterocycle may be optionally substituted by one or more hydroxyl groups, one or more alkoxy groups, one or more aryl groups, one or more halogen atoms selected from fluorine, chlorine, bromine, and iodine atoms, one or more nitro groups (—NO$_2$), one or more nitrile groups (—CN), one or more alkyl groups, with the alkyl, alkoxy, and aryl groups as defined in the context of the present invention.

The alkoxyamines of general formula (I) according to the present invention are prepared by common methods; the versatile and the most used methodology is the Atom Transfer Radical Addition (ATRA). This procedure involves the cross-coupling of an alkyl radical with a nitroxide. The alkyl radical (R$^3$.) is generated in situ by the action of a copper catalyst complexed by an amine and an alkyl halide, generally an alkyl bromide, and trapped by a nitroxide to yield an alkoxyamines [Brémond, P et al. *Chem. Commun.* 2011, 47, 4291-4293; Bertin, D. et al. *Recent Res. Devel. Org. Chem.* 2006, 10, 63-121]. Another efficient methodology is the use of metal complexes based on manganese. In this approach, the manganese complex is oxidized first into the manganese-oxo species which reacts with alkenes to afford the intermediate radical. This radical is then scavenged by the nitroxide to afford the targeted alkoxyamine after reduction.

Such compounds are chemically activable; in order to limit their cytoxicity, alkoxyamines carrying biological molecules for instance the heterocycles met in DNA strands may be prepared. They are easily biodegradable by catabolism pathways (e.g. purine and pyrimidine base derivatives) and proton-activable. In the case that the pKa is not in the physiological range, impeding the activation of alkoxyamine by protonation, the chemical activation can still be performed by pre-quaternization of the amine either by pre-oxidation or pre-alkylation [Brémond, P. et al. *Org. Lett.* 2012, 14, 358-361].

If necessary, the homolysis of alkoxyamines according to the present invention can be triggered by various processes, physical, chemical, and biological:

the physical activation of homolysis can be performed by increasing the temperature at a target value limited to 40° C. for physiological reasons, except for external applications—on skin—wherein higher temperature may be applied; the homolysis of suitable alkoxyamines can also be initiated by UV-visible irradiation when applied to external (skin) or internal (oesophagi, stomach, intestine, mucosal . . . ) membranes; homolysis of alkoxyamines may be induced by sonochemical initiation for highly selective located homolysis using focalized ultra-sounds; the physical activation of homolysis can also be induced by the radiochemical (X- or γ-ray) irradiations;

several modes of chemical activations can be used to trigger the homolysis of alkoxyamines: oxidation, acetylation, alkylation, benzylation, and complexation by a Lewis acid;

the biological activation resulting from the partial digestion of the drug by a target enzyme releases a transient alkoxyamines for which the homolysis can be enhanced by protonation or chemical rearrangement. This kind of activation represents a preferred embodiment of the present invention according to which alkoxyamines of general formula (I) are stabilized as a prodrug by grafting a chemical function sensitive to a biochemical, chemical or physical signal specific to the close environment of the tumor, leading to bioactivable alkoxyamines.

Accordingly, the present invention also relates to compounds of general formula (IIa), (IIb), (IIc), (IId), (IIe), (IIf) or (IIg):

(IIa)

(IIb)

(IIc)

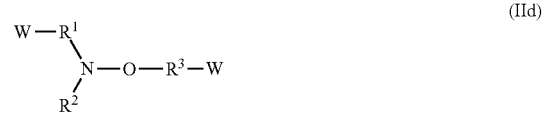

(IId)

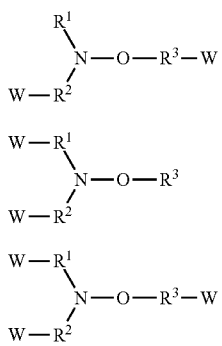

wherein R¹, R² and R³ are as defined above and
W is independently of one another selected from a peptide, a sugar, a steroid, a fatty acid, a polyketones, polyphenols, prostaglandins or a lipid, a bio-receptor or an antigen; meaning that if a general formula contains two or three groups W, each of these groups may have a different definition.

The function of a "stabilizing group" is to strengthen the bond linking the alkyl radical and the nitroxyl radical so that the homolysis is dramatically reduce affording a stable molecule. In turn, when this group is removed by chemical (e.g. hydrolysis), biological (e.g. enzymatic digestion), or physical (e.g. irradiation) methods the new alkoxyamine is highly labile. This group W is the target of specific actions that will suppress its stabilizing effect thus activate the homolysis of the alkoxyamine.

An "addressing group" targets specific cells.

Compound of general formula (IIa), (IIb), (IIc), (IId), (IIe), (IIf) or (IIg) where W is a an addressing and a stabilizing group are thus prodrugs which can be bio-activated.

Synthesis of compounds of general formula (IIa) to (IIg), bioactivatable and stable alkoxyamine derivatives which will be hydrolysed or chemically modified or modified by a physical signal to unstable alkoxyamines, depends on the biological activating signal.

The alkoxyamine compounds of general formula (I) is "stabilized" by the addition of a group W that can be chosen amongst a peptide, a sugar, a steroid, a fatty acid, a polyketones, polyphenols, prostaglandines or a lipid, or some other bio-receptors or antigens; then, the biological activating signal, for example an hydrolase (enzymes like proteases/glycosidases/lipases), hydrolyses said compound affording the subsequent alkoxyamines and, the unstable protonated alkoxyamine will homolyse in biological media.

The alkoxyamines of general formula (I) with amine function is prepared from the protected amino acids or amino function.

First, esterification and radical bromination of α-amino-ester [Narukawa, Y. et al *J. Org. Chem.* 1992, 57, 5453-5462; Hamon, D. P. G. et al. *Tetrahedron* 1990, 46, 7341-7358] afford the bromo derivative which will be engaged in ATRA coupling. Numerous examples described in the literature reported that this bromation could be realized on a tertiary carbon [Dakternieks, D. et al. *Tetrahedron: Asymmetry* 2003, 14, 3057-3068; Croft, A. K. et al. *J. Am. Chem. Soc.* 2003, 125, 4119-4124]. Moreover, radical substitution of bromo protected amino acid by a sulfur atom has been already described [Easton, C. J. et al. *Aust. J. Chem.* 1994, 47, 859-868]. Deprotection in smooth conditions (neutral for Cbz protecting group (Pd/C) [Bergmann et al. *Ber. Dtsch. Chem. Ges.* 1932, 65, 1192-1201] or in mild conditions for FMOC protecting group (piperidine) [Atherton, E. et al. *The Fluorenylmethoxycarbonyl Amino Protecting Group* in *The peptides*; Academic Press, New York, 1987, Vol 9, p 1] followed by peptide coupling reactions will afford the targeted alkoxyamines.

Compounds of general formula (IIa) to (IIg) are preferably selectively bioactivable by a specific protease, for instance a matrix metalloprotease (MMP).

The tumour itself and its environment secrete a network of active matrix metalloproteases; MMP activity is rare and non-persistent in normal tissues, its activity can thus confer the specificity of tumour targeting to the prodrug. For example, MMP may be the human gelatinases (MMP-2 and MMP-9) which are the most commonly found MMPs in tumours. Based on the chosen enzyme target, the person skilled in the art may define W with an appropriate sequence of oligopeptides; one specific and non limiting example is described by Atkinson et al. in Brit. J Pharmacology (2008) 153, 1344-1352 and relates to the oligopeptide Ac-γGlu-Pro-Cit-Gly-Hof-Tyr-Leu-.

To control that the peptide hydrolysis activates alkoxyamine, the kinetics of homolysis can be monitored by EPR.

Other biological targets include cathepsin B that is over-expressed on the surface of cancerous cells; in such a case, W may be chosen amongst Acetyl-Phenyl-Arg-; Benzyloxy-carbonyl-Phe-Arg- or Epsilon-aminocaproic acid-Leu-Cys (S-Bzl)- or many others.

Depending on compound used—of general formula (I) or of general formula (IIa) to (IIg)—and on the mode of activation, two approaches are possible for therapeutic: the "selective" and the "non-selective" approaches. Their choice will depend both on targets, aims, and preparations requirements.

The "selective" approach requires an efficient addressing of the drug combined to the chemical activation. To increase the chance of success, it is possible to combine both the addressing and the activation function by using the proteases present in the tumour environment such as matrix metalloproteinases. In such a case, only the pro-drug fraction reaching the tumour will be converted to a transient alkoxyamine activated either by protonation of a suitable amine function or by a rearrangement into a more reactive group, and will release the alkyl radicals triggering the cell death.

The "non selective" approach is used when the addressing is not possible; the efficiency of alkoxyamines as drugs relies on the fact that the tumoral cells have a higher amount of oxidant species than healthy cell but still lower than the threshold required to trigger cellular death. Then, increasing the amount of radicals in the cell would increase the imbalance of the ratio ROS/AO in such a way that the level of ROS would be high enough to cross the lethal threshold in tumoral cell whereas it is almost innocuous for healthy cells. Thus, only unhealthy cells exhibiting high level of ROS would be sensitive to the excess of generated radicals.

The present invention thus relates to compounds of general formula (I) and of general formula (IIa) to (IIg) for their use as a medicine, especially for the treatment of solid tumour—any solid tumour may be treated by this family of compounds—but also against leukemia if associated to a specific ligand or carried by an object with a specific ligand.

The delivery of said compounds in the organism may be improved by an appropriate formulation that is able to target the tumour; said formulation can consist in small particles containing alkoxyamines of general formula (I) in an environment that avoids the spontaneous homolysis of said alkoxyamines; preferably these small particles bear ligands that specifically target the tumour.

A considerable advantage of the use of compounds of general formula (I) or (IIa) to (IIg) for the treatment of cancers is that it is expected to induce recruitment of immune cells and its applicability to a broad variety of solid tumors.

Furthermore, the nitroxide part of such compounds allows the visualization and the monitoring of the curing of the tumour with Magnetic Resonance Imaging (MRI) or Electron Paramagnetic Resonance Imaging (EPRI).

The present invention also relates to pharmaceutical composition comprising at least an alkoxyamine of general formula (I) or a compound of general formula (IIa) to (IIg) and a physiologically acceptable vehicle and to a method for in vivo monitoring the curing of a solid tumor comprising the steps of:
(a) administering at least an alkoxyamine of general formula (I) or a compound of general formula (IIa) to (IIg); and
(b) visualizing the site at which prodrug activation occurs and the amount of drug deposit inside the tumour by Magnetic Resonance Imaging (MRI) enhanced by dynamic nuclear polarization or Electron Paramagnetic Resonance Imaging (EPRI).

FIG. 1 shows the viability of cells U87 treated during 1 hour with several concentrations of the tested alkoxyamine of Example I previously hydrolyzed;

FIG. 2 shows the rate of oxidative stress in U87 cells treated 1 hour with 3 mM of the alkoxyamine of Example I (ALK-1);

FIG. 3 shows the viability of cells U87 treated during 1 hour with 3 mM of the alkoxyamine of Example I with and without scavenger;

FIG. 4 shows the viability of cells U87 at several times after treatment with several concentrations of the tested alkoxyamine of Example I previously hydrolyzed.

Figure 1:
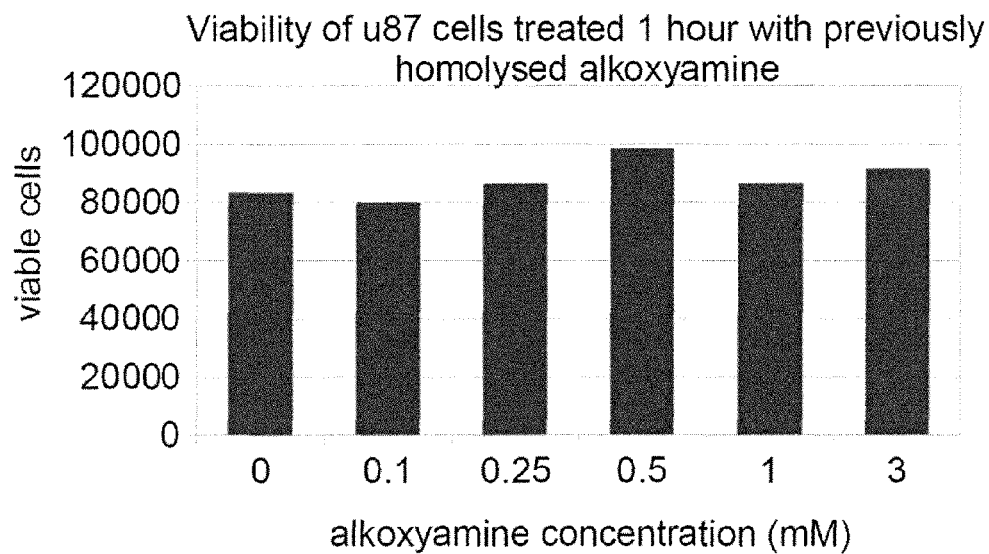
FIGS. 1 to 7 illustrate the results of assays described in Example II.
Figure 2:
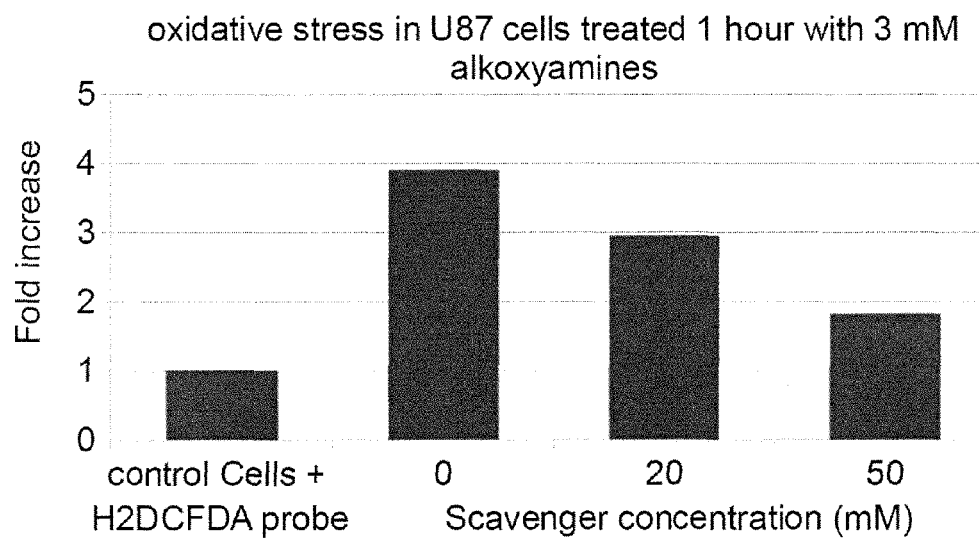
Figure 3:
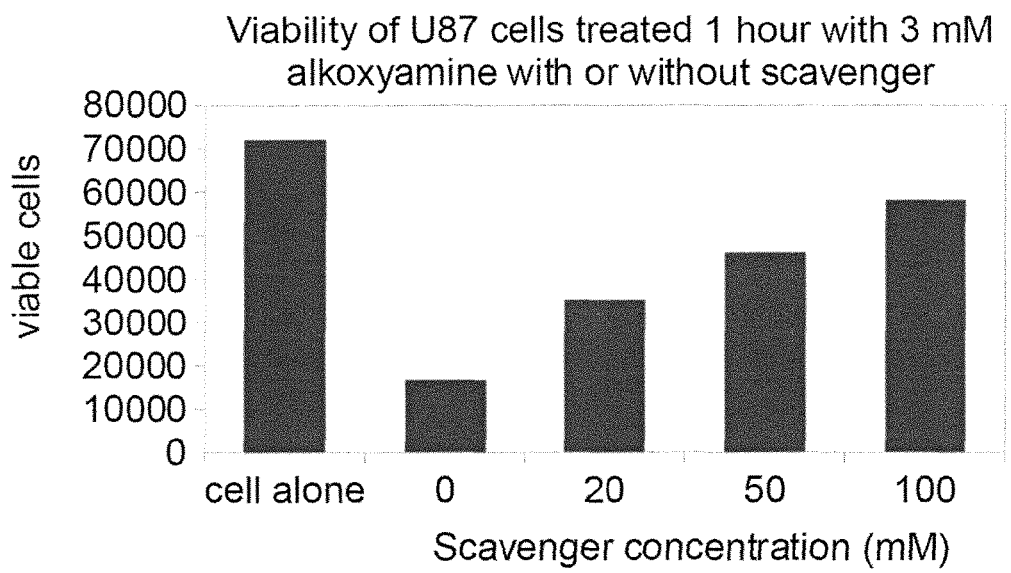
Figure 4:
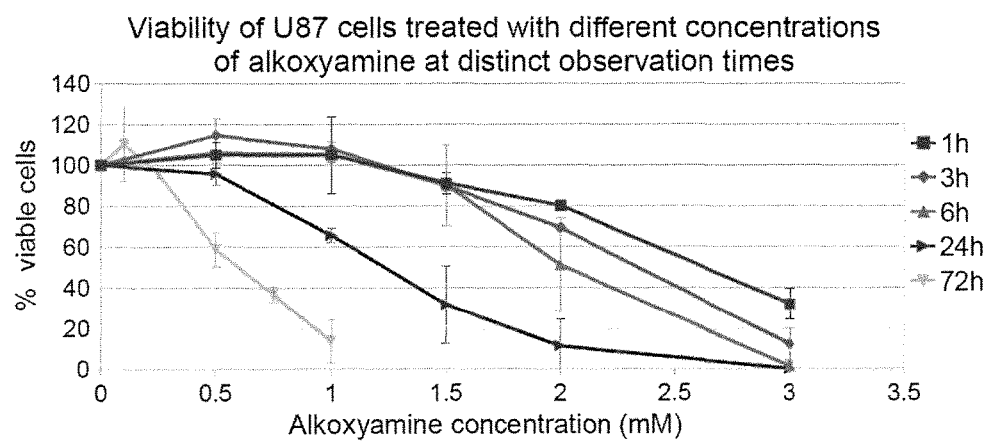
Figure 5:
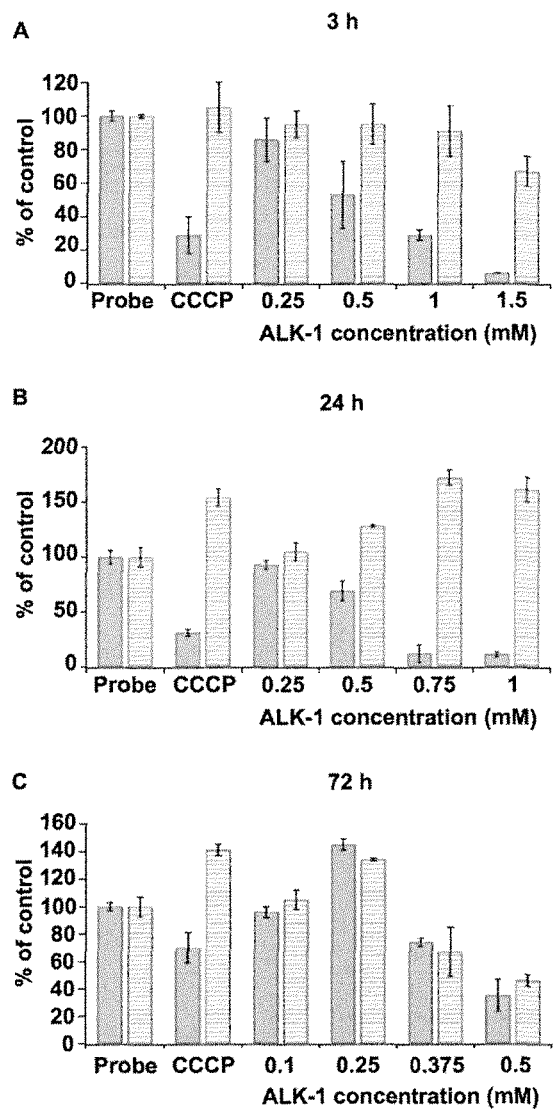
Figure 6:
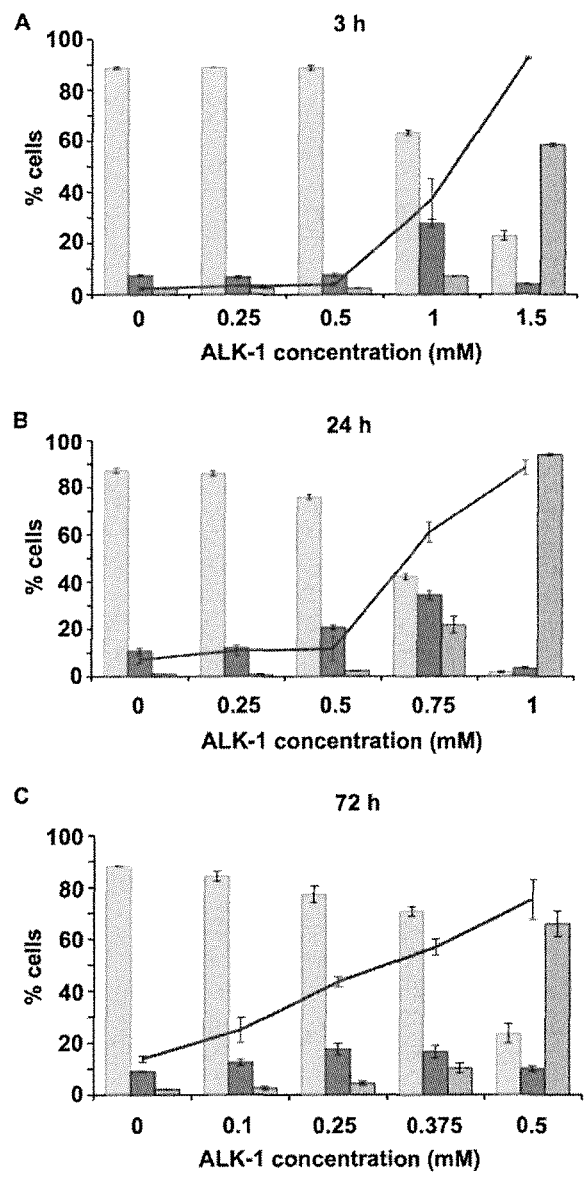

FIG. 5 illustrates mitochondria perturbations induced by ALK-1. ALK-1 effects on the mitochondria were measured using TMRE (grey bars) illustrating the variations in mitochondrial membrane potential and NAO (dashed bars) to assess the changes in mitochondrial morphology. U87 cells were incubated with concentrations of ALK-1 between 0.1 to 1.5 mM and mitochondria perturbations were observed by flow cytometry at 3 h (A), 24 h (B) or 72 h (C) observation times (n=3);

FIG. 6 illustrates Quantitative analysis of cell apoptosis induced by ALK-1 given as the percentage of U87 cells in different stages against concentrations of ALK-1 at 3 h (A), 24 h (B) and 72 h (C). Percentages of U87 cells stages were determined by PI and annexin-V staining (viable cells, IP−/AV−, grey bars; early apoptotic cells, IP−/AV+, blue bars; and late apoptotic/necrotic cells, PI+/AV+, orange bars). The percentages of positive cells for caspase activity (caspase+) were represented by the superimposed red line (−).

Figure 7:
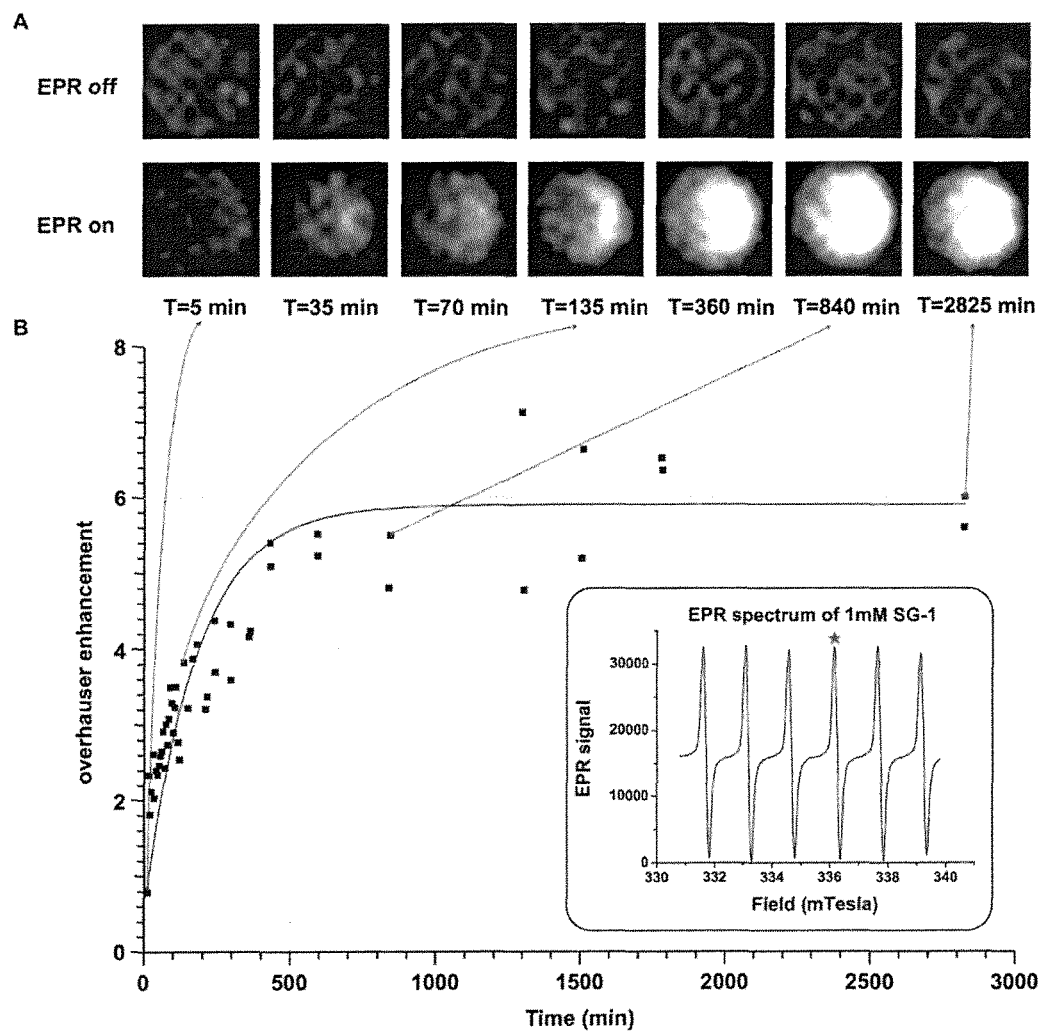

FIG. 7 illustrates the monitoring the ALK-1 homolysis by OMRI. The release of SG-1 nitroxide free radical upon 0.8 mM ALK-1 homolysis at 37° C. was monitored by Overhauser-enhanced Magnetic Resonance Imaging. (A) MRI of ALK-1 homolysis in the absence (top) or presence (bottom) of EPR irradiation. (B) Overhauser enhancement (signal with EPR on/signal with EPR off) over time. The inset shows the EPR spectrum of SG-1. The red star indicates the frequency used for EPR irradiation.

EXAMPLES

I. Synthesis of an Alkoxyamine of General Formula (I): N-methyl 4-(1-((tert-butyl(1-(diethoxyphosphoryl)-2,2-dimethylpropyl)amino)oxy)ethyl)pyridin-1-ium 4-methylbenzenesulfonate (ALK-1)

To a stirred suspension of CuBr (270 mg, 1.88 mmol, 0.55 equiv.) and Cu (239 mg, 3.76 mmol, 1.1 equiv) in degassed benzene (4.0 mL) was added N,N,N',N'',N''-pentamethyldiethylenetriamine (393 μL, 1.88 mmol, 0.55 equiv.). The resulting mixture was stirred under argon at room temperature for 30 min then a solution of 4-(1-bromoethyl)pyridine1 (700 mg, 3.76 mmol, 1.1 equiv.) and SG1 (1.0 g, 3.42 mmol, 1.0 mmol) in degassed benzene (4.0 mL) was slowly added. The mixture was stirred overnight under argon. It was then diluted with ethyl acetate, filtered and washed several times with saturated aqueous ammonia solution, water and brine. After drying with Na2SO4, filtration and concentration, column chromatography on silica gel (eluent:gradient of ethyl acetate/pentane) gave diethyl(1-(tert-butyl(1-(pyridin-4-yl)ethoxy)amino)-2,2-dimethylpropyl)phosphonate.

To a stirred solution of diethyl(1-(tert-butyl(1-(pyridin-4-yl)ethoxy)amino)-2,2-dimethylpropyl)phosphonate (500 mg, 1.25 mmol, 1.0 equiv.) in THF (12.5 mL) was added methyl sulfonate (257 mg, 1.38 mmol, 1.1 equiv.). The resulting mixture was stirred at room temperature under argon for 12 h. It was then concentrated in vacuo and triturated with an ether/pentane mixture (1/1 v/v) to give 610 mg (1.04 mmol, 83% yield) N-methyl 4-(1-((tert-butyl(1-(diethoxyphosphoryl)-2,2-dimethylpropyl)amino)oxy) ethyl)pyridin-1-ium 4-methylbenzenesulfonate:

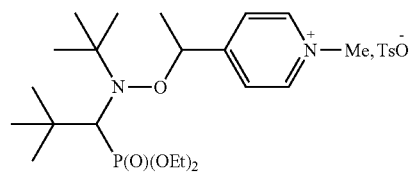

$^1$H NMR (400 MHz, CDCl$_3$): δ=9.21 (br d, J=5.3 Hz, 2H, min), 9.09 (d, J=6.0 Hz, 2H, Maj), 7.90 (d, J=6.0 Hz, 2H, Maj), 7.78 (br d, J=5.3 Hz, 2H, min), 7.73 (br d, J=8.0 Hz, 2H, min and Maj), 7.12 (br d, J=8.0 Hz, 2H, min and Maj), 6.33 (br s, 2H, min), 6.27 (d, J=13.9 Hz, 1H, Maj), 6.23 (d, J=13.9 Hz, 1H, Maj), 5.28-5.19 (m, 1H, min and Maj), 4.57 (s, 3H, min), 4.54 (s, 3H, Maj), 4.39-4.24 (m, 2H, min), 4.11-3.98 (m, 2H, min), 3.96-3.86 (m, 2H, Maj), 3.75-3.65 (m, 2H, Maj), 3.43 (d, J=27.2 Hz, 1H, Maj), 3.23 (d, J=26.4 Hz, 2H, min), 2.32 (s, 3H, min and Maj), 1.56 (d, J=6.8 Hz, 3H, min), 1.51 (d, J=6.8 Hz, 3H, Maj), 1.35-1.29 (m, 6H, min), 1.22-1.18 (m, 3H, Maj), 1.19 (s, 9H, min and Maj), 1.12 (s, 9H, Maj), 1.12 (t, J=7.1 Hz, 3H, Maj), 0.87 (s, 9H, min). $^{13}$C NMR (75 MHz, CDCl$_3$): δ=160.8, 152.7, 151.1, 148.0, 147.8, 144.5, 143.5, 142.9, 137.4, 130.6, 128.5, 127.1, 126.5, 124.4, 124.0, 121.1, 120.6, 75.7, 75.3, 68.1 (d, J=139.0 Hz), 67.5 (d, J=139.2 Hz), 60.3-59.8 (m), 58.4 (d, J=7.5 Hz), 67.6 (d, J=7.5 Hz), 34.1-33.7 (m), 29.3, 29.2 (d, J=5.8 Hz), 28.6-28.5 (m), 26.7, 22.5, 20.1, 19.8, 19.7, 15.4-14.6 (m). $^{31}$P NMR (162 MHz, CDCl$_3$): δ=24.0 (min), 23.4 (Maj). HRMS (ESI) m/z calcd for C$_{21}$H$_{40}$N$_2$O$_4$P$_1$ (M)$^+$ 415.2720, found 415.2711.

II. Use of an Alkxyamine According to Example I (ALK-1) to Kill Glioma Cells Through the Generation of a Reactive Alkyl Radical

II.A. Material & Method

Cell culture: Human glioblastoma-astrocytoma cell line U87 MG from the American Type Culture Collection (reference ATCC-HTB-14) were cultured in Dulbecco's modified eagles medium (DMEM, Gibco Corp) supplemented with 10% fetal calf serum (FCS, Gibco Corp), in a humidified atmosphere with 5% CO2 at 37° C.

Viability Test: The viability study of U87 cells treated or not with the alkoxyamine was measured by the LIVE/DEAD® Viability/Cytotoxicity Kit (Molecular Probes, Invitrogen, Life Technologies). Briefly, the cells were allowed to grow during 24 h on 24 multiwell plates (Becton-Dickinson, 2 cm$^2$/well). They were then treated with the alkoxyamine at concentrations ranging from 0.1 to 3 mM and tested for viability at distinct observation times (1, 3, 6, 24 or 72 h). To do this the adherent cells were dissociated from the plate by trypsinization and pelleted by centrifugation. Then, the cells were resuspended at 10$^6$ cells/mL on calcein-am and ethidium homodimer-1 solution during 20 minutes at room temperature and analyzed on a Guava easyCyte flow cytometer/counter (Millipore). U87 cells viability was also measured after treatment with previously homolysed alkoxyamine. For these experiments, the alkoxyamine was incubated in the culture medium during 72 h at 6 mM without the cells. U87 cells were then treated with different concentrations of this homolysed alkoxyamine for 1 h and a viability test was performed as previously described. The viability test in the presence of the free radical scavenger was carried out with an alkoxyamine concentration of 3 mM and an incubation time of 1 h. U87 cells viability was measured versus increasing concentrations the radical scavenger, trihydroxyethylrutin (Santa Cruz Biotechnology, inc.) namely, 20, 50 or 100 mM.

Oxidative stress: The cells were grown in a 24 multiwell plate as previously described. Then, cells were dissociated using 0.05% trypsin (Invitrogen, Carlsbad, Calif., USA) and suspended at a density of 1×10$^6$ cells/mL in carboxy-H$_2$DCFDA (Molecular Probes, Invitrogen, Life Technologies) at 50 µM. After 30 minutes incubation at 37° C., cells were washed with phosphate buffered saline (PBS). Cells were centrifuged and resuspended with cell culture media containing or not 3 mM alkoxyamine with or without trihydroxyethylrutin at 20 or 50 mM. After incubation time the cells were washed and analyzed on a Guava easyCyte flow cytometer/counter.

Mitochondrial alterations measurements. The red fluorescent dye tetramethylrhodamine ethyl ester (TMRE, Molecular Probes, Invitrogen, Life Technologies) was used to follow variations in mitochondrial membrane potential. This cationic probe accumulates in polarized mitochondria through the electrochemical gradient. Nonyl Acridine Orange (NAO, Molecular Probes, Invitrogen, Life Technologies) was then used as a complementary assay to assess the changes in mitochondrial morphology. Cells were plated on 24 multi-well plates (Becton-Dickinson, 2 cm$^2$/well) during 24 h and treated with a range of ALK-1 concentrations (0.1; 0.25; 0.375; 0.5; 0.75; 1.0 and 1.5 mM). After 3, 24 or 72 h, cells were resuspended in TMRE (250 nM) or NAO (500 nM) and incubated 30 minutes at 37° C., 5% CO$_2$. Incubation with 0.5 mM of Carbonyl cyanide 3-chlorophenylhydrazone (CCCP, Sigma-Aldrich) was performed as positive control of the mitochondrial depolarization staining. Then, cells were washed and analyzed by flow cytometry. All the experiments were performed three times.

Cell death analysis by annexin V/propidium iodide staining. Cell death was detected by annexin V-FITC (Molecular Probes, Invitrogen, Life Technologies) binding to exposed phosphoserine (PS) residues at the surface of cells. Cells were treated with ALK-1 at concentrations ranging from 0.1 to 1.5 mM at 37° C. and tested at distinct observation times (3, 24 or 72 h). After treatment, cells were re-suspended in staining buffer containing propidium iodide (PI, 2 µg/mL) and annexin V-FITC. Double-labeling was performed at room temperature for 15 min in darkness. Then, the percentage of viable (IP−/AV−), early apoptotic (IP−/AV+) and late apoptosis/necrotic cells (IP+/AV+) was quantified by flow cytometry. These experiments were performed twice.

Apoptosis detection through caspase-3/-7 assay. Quantitative assessment of apoptotic cells was also conducted by the detection of caspase activity using the Vybrant® FAM Caspase-3 and -7 Assay Kit (Molecular Probes, Invitrogen, Life Technologies). Briefly, cells were treated with the previously described ALK-1 concentrations during 3, 24 or 72 h. After the alkoxyamine treatment, the cells were dissociated from the support, washed and incubated 1 h at 37° C. in FLICA working solution. Then, the cells were washed and green fluorescence was measured by flow cytometry. These experiments were performed twice.

Overhauser-Enhanced Magnetic Resonance Imaging.

EPR Cavity and MRI devices. The OMRI experiment were done in a C-shaped 0.2 T MRI system (Magnetom Open Viva, Siemens, Erlangen, Germany) and a resonant TE011 transverse electric mode EPR cavity setup (Bruker, Wissembourg, France) as described previously. The EPR cavity, placed at the center of the magnet, was used to saturate the electron spin transition of the nitroxide SG1 produced upon ALK-1 homolysis. A homemade saddle-shaped MRI coil (28 mm in diameter and 29 mm in length) in the EPR cavity was used for imaging.

Electron spin saturation was carried out at 5.4573 GHz, corresponding to the first line at high field from the center of the EPR spectrum. The proton frequency was 8.24 MHz. Sample temperature was kept at 37° C.

OMRI experiments were performed in two NMR tubes (4 mm inner diameter): one containing 0.8 mM of SG1 nitroxide in phosphate buffer saline (not shown) and the other with 0.8 mM of ALK-1 in DMEM, 10% FCS. ALK-1 homolysis was followed for 48 hours.

Pulse sequences. 2D MRI images were acquired with a standard gradient echo sequence, which was synchronized to an external pulse generator for electron spin saturation. The EPR pulse time was 260 ms long, followed immediately by the MRI sequence. This sequence had the following parameters: TE (echo time)=10 ms; TR (repetition time) minimal=27 ms; Effective TR=300 ms; Field of view=22×22 mm; Matrix size=64×64; Slice thickness=5 mm; Spatial resolution=0.34×0.34 mm, Number of averages=2 and an acquisition time=22 s. All MR adjustments were done manually, using the same fixed receiver amplification gain for both measurements, without ($S_{off}$) and with ($S_{on}$) HF irradiation, so that signals can be directly compared and Overhauser enhancements ($S_{on}/S_{off}$) calculated.

Post-processing. All signal intensity measurements were made with ImageJ imaging software (ImageJ, National Institutes of Health, USA). Signal intensity was measured in a rectangular region of interest of 2 mm$^2$ positioned in the NMR tube area. Curve fitting and $t_{1/2}$ measurement were carried out with IGOR Pro (Wavemetrics, Lake-Oswego, Oreg., USA).

II.B. Results

N-methyl 4-(1-((tert-butyl(1-(diethoxyphosphoryl)-2,2-dimethylpropyl)amino)oxy)ethyl)pyridin-1-ium 4-methylbenzenesulfonate (ALK-1) has an homolysis half-life time of 50 mn at 37° C.; 3 mM of this compound is applied one hour to U87 glioblastoma cell cultures in the presence of increasing concentrations of a non toxic polyphenolic free radical scavenger. The viability of the cells was then measured by cytometry with the combined ethidium bromide/calcein tests. The viability diagram shows that at one hour (one half-life of the alkoxyamine) 3 mM of this alkoxyamine kills approximately 75% of the cells.

However most of the cells (80%) can be saved by the free radical scavenger. This strongly suggests that cell death occurs through a free radical mechanism. This conclusion is further strengthened by observing the oxidative stress created by 3 mM alkoxyamine at one hour with the intracellular probe H2DCFDA.

The results (see FIGS. 1 to 4) clearly demonstrate that cell death occurs through an oxidative stress which is suppressed by the free radical scavenger. It is also correlated to the fact that alkoxyamines at the same concentration but previously homolysed do not carry any toxicity for U87 cells confirming that the freshly produced reactive alkyl radical is required to kill the cells. These preliminary results show that the concept works even with a slow homolysing alkoxyamine at reasonable concentrations generating low transient free radical concentrations.

Mitochondria modifications. To address the ALK-1 effect on mitochondria, the mitochondrial potential was monitored using tetramethylrhodamine ester (TMRE). In addition, the mitochondrial morphology changes were observed through cardiolipin accessibility by nonyl acridine orange (NAO) staining. For all the tested times of incubation, the CCCP (carbonyl cyanide 3-chlorophenylhydrazone) uncoupling agent generated the expected drop of the mitochondrial potential (FIG. 5). Independently of the incubation time the effect of CCCP on the accessibility of the cardiolipins to the NAO appeared either neutral or positive. Starting from 0.5 mM ALK-1, the mitochondrial potential drops for all times of observation (FIG. 5A-C). Nevertheless, NAO staining displays diverging evolutions as a function of ALK-1 concentration at 24 h (FIG. 5B) and 72 h (FIG. 5C) of incubation. Indeed at 24 h, NAO staining increased for ALK-1 concentrations greater than 0.5 mM while the potential dropped. At 72 h, NAO staining evolution correlates with the mitochondrial potential variations. Commonly, the cardiolipin labeling is described as a mitochondrial mass marker. However, it also depends on the cardiolipin accessibility therefore it reflects the mitochondria morphology. A drop of both cardiolipin labeling and the mitochondrial potential suggests a loss of the mitochondrial content as observed after 72 h incubation in the presence of 0.375 to 0.5 mM (FIG. 5C). An increase of NAO staining associated to a decrease of the mitochondrial potential is better discussed as a change in the mitochondrial morphology as seen at 24 h between 0.5 and 1 mM (FIG. 5B). This is consistent with the fact that the mitochondrial content could not increase within 24 h especially on a stressful situation. A simultaneous increase of both parameters at 72 h and 0.25 mM reveals a transient growth of the mitochondrial mass compatible with the observation time (FIG. 5C).

Apoptosis induction by ALK-1. U87 cells were treated with ALK-1 at various concentrations and observed at 3, 24 and 72 h. Then, cell apoptosis was studied looking at propidium iodide membrane permeability (PI), phosphatidyl serine translocation by annexin-V (AV) staining and caspase-3 and -7 activation (FIG. 6). PI and annexin-V staining discriminate the early apoptotic cells (PI−/AV+) from the late apoptotic/necrotic cells (PI+/AV+). Caspase activation would discriminate the necrotic cells (caspase−) from the apoptotic cells (caspase+). At 3 h (FIG. 5A), the percentage of PI−/AV+ cells increased until 1 mM of alkoxyamine treatment. At 1.5 mM most cells were necrotic or apoptotic cells (PI+/AV+). Percentage of cells carrying activated caspases reached 92% at 1.5 mM ALK-1. At 24 h (FIG. 5B), the percentage of PI−/AV+ cells increase from 0.5 mM to 0.75 mM ALK-1. At 1 mM, 94% of the cells were necrotic or apoptotic cells (PI+/AV+). Simultaneously, 88% of the cells were caspase positive. At 72 h (FIG. 5C), a slight rise in the level of PI−/AV+ cells was observed at 0.25 mM and 0.375 mM of ALK-1. At 0.5 mM, most cells were PI+/AV+. At this observation time, the number of caspase positive cells varies almost linearly from the lowest ALK-1 concentration of 0.1 mM to reach 80% at 0.5 mM. From the time dependent study, two ALK-1 concentrations appeared noticeable. At 0.25 mM for the 24 h observation time cells did not seem to enter the apoptotic pathway (most cells are PI−/AV− and caspase−). However at 72 h, cells displayed early apoptotic properties and were more than 40% caspase+. At 0.5 mM, cells entered into apoptosis no later than 24 h and after 72 h the remaining cells were massively in late apoptotic state with 80% of the cells being caspase+. These results demonstrated that ALK-1 induced the U87 cells death through apoptosis. It is worth to note that ALK-1 action ended after 5 times the half-life of homolysis, namely 5 hours. However, apoptosis appeared much later for the lowest concentrations. This strongly suggests that some irreversible alterations occurred within five hours which were able to trigger apoptosis between 24 to 72 h after the beginning of alkoxyamine treatment.

Imaging of ALK-1 homolysis by OMRI. The homolysis of ALK-1 was followed by OMRI at 0.8 mM in culture cell medium at 37° C. The signal enhancement due the generated nitroxide radical was monitored for 47 h (FIG. 7). The signal amplification increased from 1-fold at 5 mM to 6-fold at 2825 min after the beginning of ALK-1 homolysis. The signal displays an asymptotic exponential growth as expected from the first order kinetics of homolysis and was thus fitted to the equation (1):

$$y = y_0 - A \times e^{-kt} \quad (1)$$

with $y_0=5.9\pm0.2$; $A=5.3\pm0.3$ and $k=5.6 \cdot 10^{-3}$ min$^{-1}$. The experimental $t_{1/2}$ was approximately 125 min. This $t_{1/2}$ was fairly close to the value calculated from the homolysis activation energy. It afforded $E_a=109$ kJ/mol, very close to the 106 kJ/mol reported, taking into account the inaccuracy of the technique. The 2.5 times discrepancy is easily accounted for by the non-linear response of whole OMRI process due to the non-linear effect of the concentration of the nitroxide on the Overhauser enhancement and due to the lack of stability of the actual setup over 48 hours. These results demonstrated that the released nitroxide can be used as a reporter of the radical alkyl owing to the one-to-one stoechiometry.

Although alkoxyamine ALK-1 was only an unrefined lead-compound, it displays a dose-dependent cytotoxic effect. This effect occurs through its homolysis and we showed that an in situ-released alkyl radical was required to induce cell death. Indeed, when the alkyl radical was scavenged, cell viability turned back to normal level. Several effects of alkoxyamines on cells that could lead to cell death were investigated. ALK-1 induced a strong oxidative stress which was also suppressed upon alkyl radical scavenging. Even at low concentrations persistent changes in the mitochondrial potential, mass and/or morphology were observed. Ultimately, as shown by the caspase-3 and -7 activation, membrane integrity alteration and phosphatidyl serine translocation cell death occurred by the apoptotic pathway.

The observation of the viability versus the time after exposition to ALK-1 revealed a delayed toxicity, as compared with the completion of homolysis (about 5 h) and the life-time of the alkyl radical (a few milliseconds). This suggests that the released alkyl radical promptly induced cell alterations that committed the cells into an irreversible cell death process. The various time scales observed for oxidative stress, mitochondrial alterations and the development of cells apoptosis suggest the absence of a single sequential link between these phenomena. It rather indicates a direct action from the alkyl radical on each effect without excluding interactions.

It has been shown here that the nitroxide radical released from the alkoxyamine homolysis could be efficiently detected by OMRI. This method is currently developed in order to enhance MRI specificity. The nitroxide stability would allow the monitoring of alkoxyamine homolysis in vivo, with an accurate real-time localization in 3D. Moreover, a longitudinal follow-up of the treatment could be achieved through standard MRI modality.

The invention claimed is:

1. Compound of general formula (IIa), (IIb), (IIc), (IId), (IIe), (IIf) or (IIg):

$$R^1 \diagdown N-O-R^3-W \quad \text{(IIa)}$$
$$R^2 \diagup$$

$$W-R^1 \diagdown N-O-R^3 \quad \text{(IIb)}$$
$$R^2 \diagup$$

$$R^1 \diagdown N-O-R^3 \quad \text{(IIc)}$$
$$W-R^2 \diagup$$

$$W-R^1 \diagdown N-O-R^3-W \quad \text{(IId)}$$
$$R^2 \diagup$$

$$R^1 \diagdown N-O-R^3-W \quad \text{(IIe)}$$
$$W-R^2 \diagup$$

$$W-R^1 \diagdown N-O-R^3 \quad \text{(IIf)}$$
$$W-R^2 \diagup$$

$$W-R^1 \diagdown N-O-R^3-W \quad \text{(IIg)}$$
$$W-R^2 \diagup$$

wherein
$R^1$ and $R^2$ which may be identical or different are chosen from:
a secondary alkyl group $$\overset{X}{\underset{Y}{\diagdown}}\!\!-$$

or a tertiary alkyl group $$Y-\overset{X}{\underset{Z}{\mid}}\!\!-$$

wherein X, Y and Z which may be identical or different are chosen amongst a linear or ramified alkyl radical including short and long carbon chains having from 1 to 40 carbon atoms, X, Y and/or Z may be substituted by a functional group chosen from hydroxyl, amine, mercaptan, azide, halogenure, carbonyl chosen from the group consisting of: aldehyde, amide, ketone, acid, ester, and their thio derivatives, aromatic, heteroaromatic, heterocycles, vinyl, alkyne, phosphoryl optionally substituted by a ($C_1$-$C_4$) alkoxy radical;
a 5 to 12 membered ring, said ring being heterocyclic or not, which can carry the various functions mentioned above;

wherein $R^1$ and/or $R^2$ are optionally substituted by a stabilizing group or an addressing group W selected from the group consisting of: peptides, sugars, steroids, fatty acids, polyketones, polyphenols, prostaglandins, lipids, bio-receptors, and antigens;

$R^1$ and $R^2$ being different from $R^3$;

$R^3$ is chosen from:
(i) a secondary alkyl radical $$\overset{X}{\underset{Y}{\diagdown}}\!\!-$$

or a tertiary alkyl radical $$Y-\overset{X}{\underset{Z}{\mid}}\!\!-$$

wherein X, Y and Z may be identical or different, X and Z are a linear or ramified alkyl radical including short and long carbon chains having from 1 to 40 carbon atoms and may be substituted by a functional group chosen from hydroxyl, amine, mercaptan, azide, halogenure, carbonyl chosen from the group consisting of: aldehyde, amide, ketone, acid, ester, and their thio derivatives, aromatic, heteroaromatic, heterocycles, vinyl, alkyne; Y is chosen from an aromatic group or heteroaromatic group, a carbonyl function optionally in a protected form such as enol, acetate, acetals, enamine, an easily oxidable function, a vinyl, an alkene function including short and long carbon chains having from 1 to 40 carbon atoms, an alkyne function including short and long carbon chains having from 1 to 40 carbon atoms, a function thiocarbonyl, a function imine, a function oxime or a function cyano;

$$\overset{Z_1}{\underset{Z_3}{\diagup}}\!\!=\!\!\overset{Z_2-G}{\diagdown} \quad \text{(ii)}$$

wherein
$Z_1$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function —CO—, a thiocarbonyl function —CS—, an amine or an imine function —C(NH)— or —C(N—[$C_1$-$C_4$ alkyl])- or an oxime function —C(NOH)—;

$Z_2$ is selected from a single bond, —O—, —S—, —NR—, with R being a linear or ramified $C_1$-$C_{40}$ alkyl radical, a aryl or a heteroaryl group, a linear or ramified $C_1$-$C_{40}$ vinyl radical, a linear or ramified $C_1$-$C_{40}$ alkyne radical, those radicals being optionally substituted by a carbonyl function —CO—, a thiocarbonyl function —CS—, an amine or an imine function —C(NH)— or —C(N—[$C_1$-$C_4$ alkyl])- or an oxime function —C(NOH)—;

$Z_3$ is selected from a hydrogen atom; a linear or ramified $C_1$-$C_{40}$ alkyl radical, a linear or ramified $C_1$-$C_{40}$ vinyl radical, a linear or ramified $C_1$-$C_{40}$ alkyne radical, an aryl group, a heteroaryl group, those radicals being optionally interrupted by at least one O, S, NH and optionally substituted by a carbonyl function —CO—, a thiocarbonyl function —CS—, an amine or an imine function —C(NH)— or —C(N—[$C_1$-$C_4$ alkyl])- or an oxime function —C(NOH)—;

G is either a hydrogen atom or an addressing or stabilizing group W selected from the group consisting of: peptides, sugars, steroids, fatty acids, polyketones, polyphenols, prostaglandins, lipids, bio-receptors, and antigens;

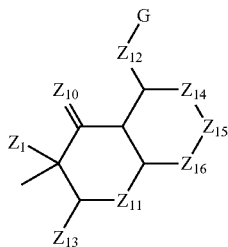

(iii)

wherein $Z_1$ and G are as described above;
$Z_{10}$ and $Z_{11}$ are independently selected from —O—, —S—, —NR— and —$CR_2$- where R is as defined above;
$Z_{12}$ is selected from —O—, —S— and —NR— where R is as defined above;
$Z_{13}$ is selected from —$OSO_2$R, a halogen atom, an ammonium group, a phosphate group, —$RSO_2$, —OH, —SH, —OR and —SR where R is as defined above;
$Z_{14}$ $Z_{15}$ and $Z_{16}$ are independently selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function —CO—, a thiocarbonyl function —CS—, an amine or an imine function —C(NH)— or —C(N—[$C_1$-$C_4$ alkyl])- or an oxime function —C(NOH)—;

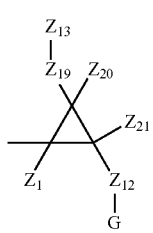

(iv)

wherein $Z_1$ $Z_{12}$ $Z_{13}$ and G are as described above;

$Z_{19}$ is selected from —$CH_2$—, —CHR— and —$CR_2$— where R is as defined above;
$Z_{20}$ and $Z_{21}$ are independently selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally interrupted by at least one O, S, NH and optionally substituted by a carbonyl function —CO—, a thiocarbonyl function —CS—, an amine or an imine function —C(NH)— or —C(N—[$C_1$-$C_4$ alkyl])- or an oxime function —C(NOH)— and wherein W is independently of one another selected from the group consisting of: peptides, sugars, steroids, fatty acids, polyketones, polyphenols, prostaglandins, lipids, bio-receptors, and antigens.

2. Compounds according to claim 1 wherein $R^3$ is selected from:

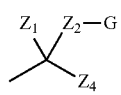

(v)

wherein $Z_1$, $Z_2$ and G are as described previously;
and $Z_4$ is chosen from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—);

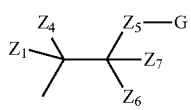

(vi)

wherein $Z_1$, $Z_4$, R and G are as described previously;
$Z_5$ is selected from —O—, —S—, —NH— and —NR— where R is as defined above;
$Z_6$ is chosen from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—); and
$Z_7$ is selected from —OR, —SR, —OH and —SH where R is as defined above;

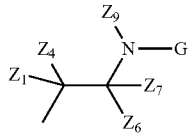

(v)

wherein $Z_1$, $Z_4$, $Z_6$ and G are as described above;

$Z_8$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) and an oxime function (—C(NOH)—); and $Z_9$ is selected from —H and —R where R is as defined above;

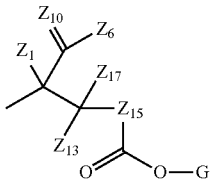
(vi)

wherein $Z_1$, $Z_6$, $Z_{10}$, $Z_{13}$ and G are as described above;

$Z_{17}$ is selected from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally interrupted by at least one O, S, NH and optionally substituted by a carbonyl function (—CO—), a thiocarbonyl function (—CS—), an amine or an imine function ((—C(NH)— or —C(N—[$C_1$-$C_4$ alkyl])-), an oxime function (—C(NOH)—) ; an aryl or a heteroaryl group optionally linked to at least one O, S, NH;

$Z_{18}$ is selected from —O—, —S—, —NH—, —NR—, —CH$_2$—, —CHR— and —CR$_2$— where R is as defined above;

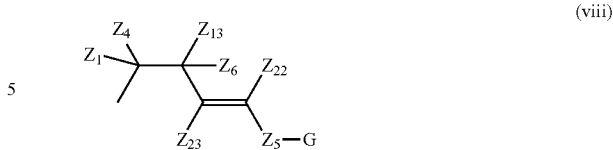
(viii)

wherein $Z_1$, $Z_4$, $Z_5$, $Z_6$, $Z_{13}$ and G are as described above;

$Z_{22}$ and $Z_{23}$ are selected independently from a hydrogen atom, a linear or ramified $C_1$-$C_{40}$ alkyl radical, a linear or ramified $C_1$-$C_{40}$ alkene radical, a linear or ramified $C_1$-$C_{40}$ alkyne radical, an aryl group, a heteroaryl group, those radicals being optionally substituted by a carbonyl function (—CO—), a thiocarbonyl function (—CS—), an amine or an imine function (—C(NH)— or —C(N—[$C_1$-$C_4$ alkyl])-) or an oxime function (—C(NOH)—).

3. Pharmaceutical composition comprising at least one compound according to claim 1 and a physiologically acceptable vehicle.

4. Method for in vivo monitoring the curing of a solid tumor comprising the steps of:
(a) administering at least a compound according to claim 1; and
(b) visualizing the site at which prodrug activation occurs and the amount of drug deposit inside the tumor by Magnetic Resonance Imaging (MRI) enhanced by dynamic nuclear polarization or Electron Paramagnetic Resonance Imaging (EPRI).

5. Method for treating a solid tumor comprising the step of:
administering a therapeutically effective amount of a compound of claim 1 to a subject in need thereof.

* * * * *